United States Patent [19]

Kyozuka

[11] Patent Number: 4,569,356
[45] Date of Patent: Feb. 11, 1986

[54] METHOD AND APPARATUS FOR DETECTING FETAL HEART RATE BY AUTOCORRELATION

[75] Inventor: Shigeyuki Kyozuka, Tokyo, Japan

[73] Assignee: Nihon Kohden Corporation, Tokyo, Japan

[21] Appl. No.: 668,031

[22] Filed: Nov. 5, 1984

[51] Int. Cl.⁴ .............................................. A61B 5/04
[52] U.S. Cl. .................................... 128/698; 128/663
[58] Field of Search ...................... 128/698, 660, 663; 73/861.06; 324/77 G

[56] References Cited

U.S. PATENT DOCUMENTS

| | | | |
|---|---|---|---|
| 3,157,781 | 11/1964 | Gruen | 324/77 G |
| 3,717,756 | 2/1973 | Stitt | 324/77 H |
| 3,982,528 | 9/1976 | Phillipps | 128/661 |
| 3,991,365 | 11/1976 | Takeuchi | 324/77 G |
| 4,037,151 | 7/1977 | Takeuchi | 128/698 |
| 4,239,048 | 12/1980 | Steuer | 364/417 |
| 4,346,840 | 8/1982 | Poston et al. | 324/77 G |
| 4,403,184 | 9/1983 | Witt et al. | 128/695 |
| 4,494,213 | 1/1985 | Thompson | 73/861.06 |

FOREIGN PATENT DOCUMENTS 522507 10/1976 U.S.S.R. ............................ 324/77 G

OTHER PUBLICATIONS

Takeuchi et al., "An Adaptive Correlation Rate Meter: A New Method for Doppler Fetal Heart Rate Measurements", *Ultrasonics*, May 1978, vol. 16, No. 3, pp. 127–137.

Courtin et al., "A Versatile, Semiautomatic Fetal Monitor for Non Technical Users", *Hewlett-Packard Journal*, Jan. 1977, vol. 28, No. 5, pp. 16–23.

Primary Examiner—William E. Kamm
Assistant Examiner—Mitchell J. Shein
Attorney, Agent, or Firm—Hoffmann, Dilworth, Barrese & Baron

[57] ABSTRACT

A fetal heartbeat signal detected by the principle of an ultrasonic Doppler effect is autocorrelated, and a fetal heart rate is detected from the periodicity of peaks of a determined autocorrelation function. In such a process, peaks of the autocorrelation function are detected, and a peak truly indicative of the fetal heart rate is detected from closeness of righthand inclinations of the peaks to a righthand inclination of the origin of the autocorrelation function.

15 Claims, 11 Drawing Figures

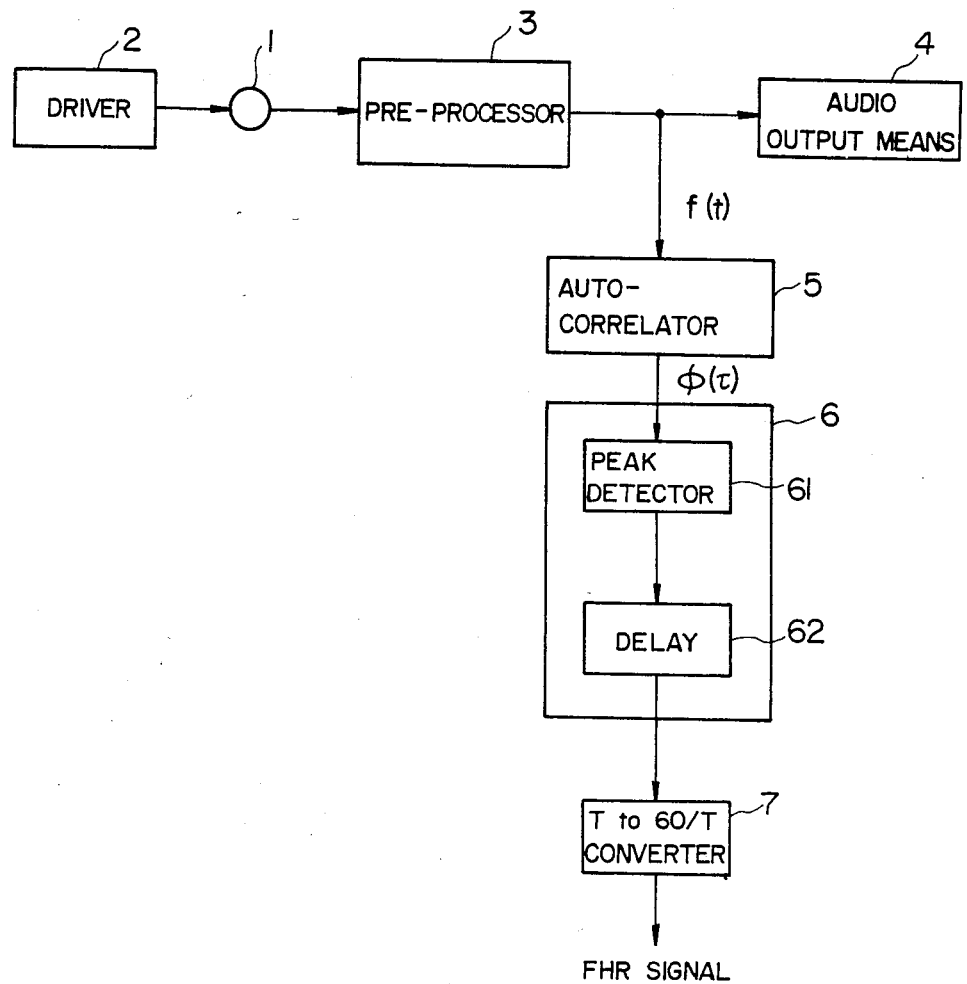

METHOD AND APPARATUS FOR DETECTING FETAL HEART RATE BY AUTOCORRELATION

BACKGROUND OF THE INVENTION

The present invention relates to a method and apparatus for detecting a fetal heart rate by autocorrelating an ultrasonic Doppler signal reflected from a fetal heart and then detecting the fetal heart rate based on the periodicity of the autocorrelation curve.

To monitor the well-being of a fetus in the process of the delivery, it is highly effective to simultaneously and continuously record a fetal heart rate curve and a labor curve. One known process of measuring the fetal heart rate (hereinafter referred to as "FHR") is composed of the steps of emitting an ultrasonic wave toward a fetal heart and utilizing a reflected ultrasonic Doppler signal which has been subjected to a frequency shift. However, since such an ultrasonic Doppler signal representative of one heart beat is quite complex due to complicated beating of the heart, it has been difficult to detect a train of pulses which are precisely synchronous with the corresponding fetal heart beats.

U.S. Pat. No. 3,982,528 discloses an apparatus for detecting the FHR by autocorrelation technique to eliminate the above problem. FIG. 1 of the accompanying drawings is a block diagram of the disclosed apparatus. Included in the apparatus is an ultrasonic transducer 1 and a driver 2 for the ultrasonic transducer 1. A pre-processor 3 is provided and includes an amplifier, AM detector, and a filter for detecting a frequency-shifted signal from a received signal from the transducer 1. An audio output means 4 produces an audio output indicative of a fetal heartbeat signal f(t) issued from the pre-processor 3, and an autocorrelator 5 autocorrelates the output signal f(t) from the pre-processor 3. A post-processor 6 detects the periodicity of a pattern of autocorrelation function signal $\phi(\tau)$ generated by the autocorrelator 5. A pulse-interval-to-heart-rate converter 7 issues a step-like signal by calculating a heart rate 60/T (heartbeats/minute) from a time interval T sec. of a train of pulses generated by the post-processor 6.

The post-processor 6 comprises a peak detector 61 for detecting a new peak by comparing the level of the signal $\phi(\tau)$ and a level related to its immediately prior peak, and a delay means 62 for issuing a peak signal only when there is no next peak detected within a predetermined time after the peak has been detected by the peak detector 61. The autocorrelator 5 supplied with the output signal f(t) (FIG. 2A) from the pre-processor 3 autocorrelates the supplied signal in a digital manner, converts the processed signal into an analog signal, and then issues the analog signal $\phi(\tau)$ (indicated by the solid line in FIG. 2B).

The peak detector 61 compares the immediately prior peak reference level (indicated by the dotted line in FIG. 2B) with the signal $\phi(\tau)$ to detect the peak (FIG. 2C). The delay means 62 issues the pulse signal (indicated by the solid line in FIG. 2D) to the converter 7 when no next peak is detected in the predetermined time after the peak has been detected. The converter 7 issues the step-like FHR signal (indicated in FIG. 2E on a compressed time base) of the level corresponding to the interval of the pulse signal.

As shown in FIG. 2A, the fetal heartbeat signal obtained by the ultrasonic Doppler process frequently contains a few waveforms synchronous with heartbeats per heartbeat. This is because movements of the heart valves, heart wall, blood flow, and others are detected as signals when the heart is beating. When the autocorrelation function is calculated under such condition, there appear false peaks other than the true peak used for detecting a heart rate, resulting in a tendency to cause an error in detecting the true peak. Such an error is also caused by signal noise. More specifically, as shown in FIG. 2B, the signal $\phi(\tau)$ usually contains false peaks b, c before and after the true peak (hereinafter referred to as a "main max.").

When the peak detector 61 detects the main max. a and the peak b before the main max. a, the delay means 62 issues only a proper peak signal indicative of the main max. a. However, if the peak b is of a level exceeding the main max. a, then the main max. a does not necessarily reach the peak reference level, and cannot be detected. If the detected level of the peak c is high, then the delay means 62 responds to the peak c and issues a false peak signal which is delayed from the main max. a. Furthermore, it is impossible to discriminate the main max. from high-level noise. Therefore, the known apparatus for detecting FHR signals has had limited accuracy.

SUMMARY OF THE INVENTION

It is an object of the present invention to provide a method and apparatus for improving the accuracy of detection of FHR by autocorrelating a fetal heartbeat signal detected through an ultrasonic Doppler effect.

It is found that the inclinations or slopes of main maximums appearing successively with time delays and the righthand inclination or post main maximum slope of the origin $\phi(\tau)$ of an autocorrelation function signal are similar to each other since fetal heart beat signals at least close to each other are similar to each other in amplitude and period. However, the righthand inclinations or slope of the origin is generally different from the righthand inclination of false peaks b, c, and the righthand inclination of a false peak which is highly noisy is less similar to the righthand inclination of the origin.

More generally, an autocorrelation function curve of an original signal which has periodically similar waveforms has periodic peaks. And based on this fact, a peak having a righthand inclination similar to the righthand inclination in the vicinity of the origin can be detected.

According to the present invention, peaks of an autocorrelated function signal are first detected, and the righthand inclinations of the original of the function and the peaks are calculated. A main max. is determined by ascertaining whether the peak inclinations are similar to the righthand inclination of the origin, and a delay time between the origin and the first main max. thus determined is employed as a heartbeat interval.

The above and other objects, features and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 1 is a block diagram of the conventional FHR detecting apparatus;

DESCRIPTION OF THE PREFERRED EMBODIMENT

Figure 2A:
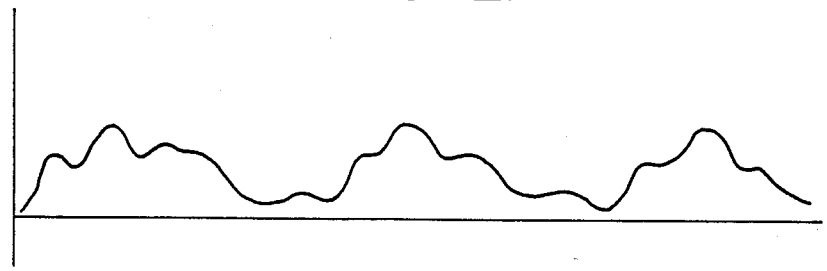
FIGS. 2A–2E are a series of diagrams showing the waveforms of signals generated in the apparatus of FIG. 1.
Figure 2B:
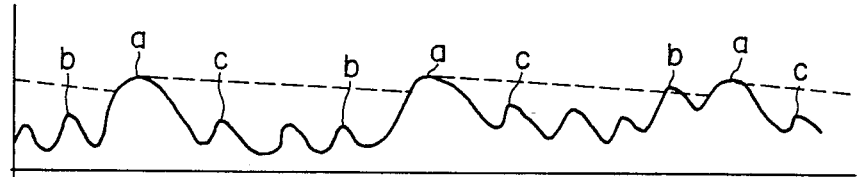
Figure 2C:
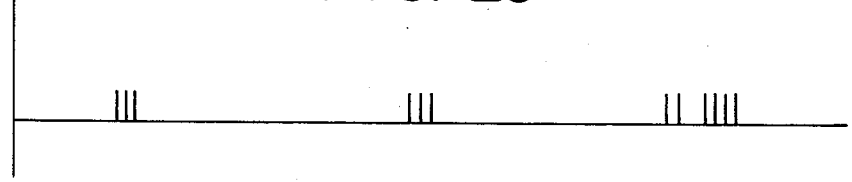
Figure 2D:
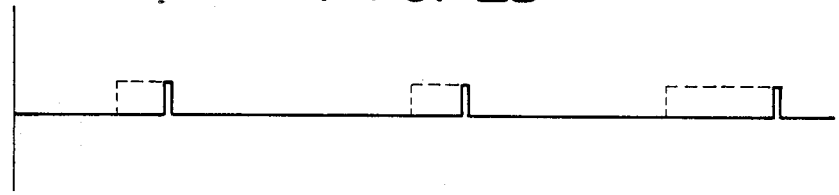
Figure 2E:
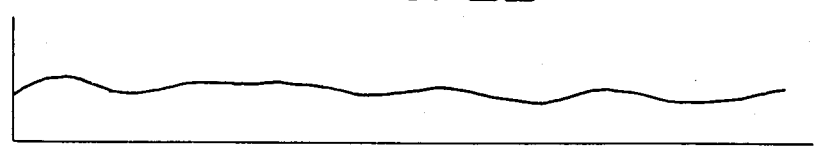
Figure 3:
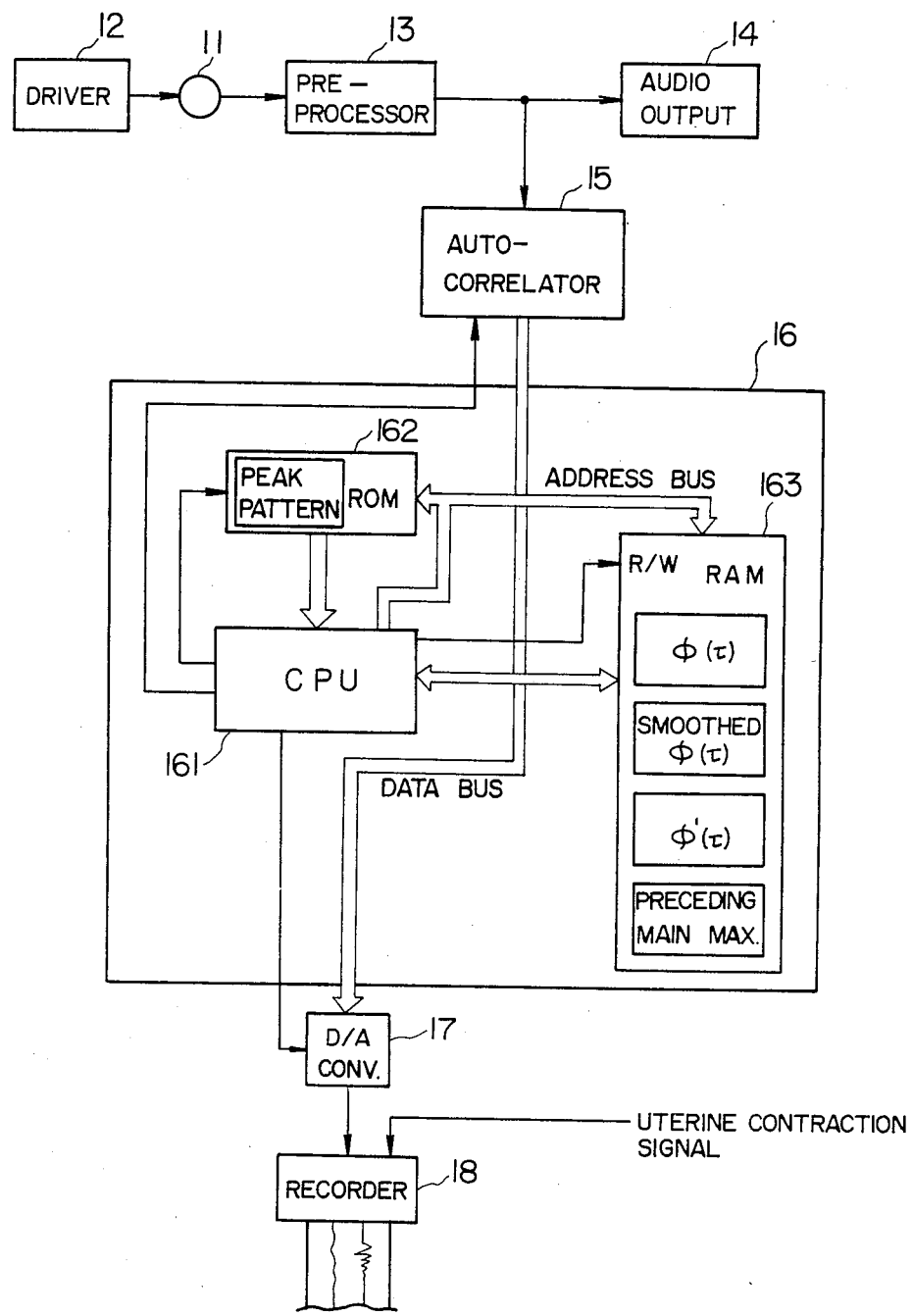
FIG. 3 is a block diagram of an FHR detecting apparatus according to the present invention.

FIG. 3 illustrates in block form an FHR detecting apparatus according to the present invention. The FHR detecting apparatus includes a transducer 11, a driver 12, a preprocessor 13, and an audio output means, which all perform the same functions as those described with reference to FIG. 1. The FHR detecting apparatus also includes a D/A converter 17 for converting a digital signal, indicative of a heart rate determined by a microcomputer 16 (described later) into an analog signal, and a recorder 18 for continuously recording an FHR signal generated by the D/A converter 17 and a labor signal detected by a tocometer (not shown). An autocorrelator 15 may be in the form of a digital circuit which is known from U.S. Pat. No. 3,717,756, or a microcomputer.

The microcomputer 16 serves as a post-processor for detecting the period of a heartbeat from an output signal from the autocorrelator 15. The microcomputer 15 is mainly composed of a CPU 161, a ROM 162 storing a program for operating the CPU 161, and fixed data, and a RAM 163 for storing data as they are autocorrelated.

The auto correlator 15 samples a fetal heart beat signal f(t) at intervals of 5 ms for autocorrelation. The CPU 161 reads an autocorrelation function signal $\phi(\tau)$ from the autocorrelator 15 at intervals of 320 ms and stores the signal at $\phi(\tau)$ area having 256 addresses and 8 bits corresponding to the signal resolution.

Figure 4:
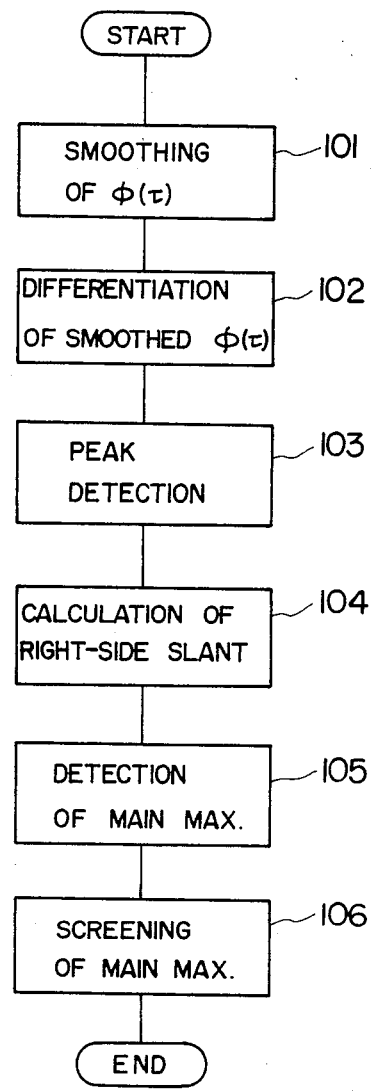
FIG. 4 is a flowchart showing operation of a post-processor in the apparatus of FIG. 3.

The microcomputer 16 post-processes the signal $\phi(\tau)$ according to the flowchart of FIG. 4 repeatedly at the period of 320 ms. In a step 101, the CPU 161 reads data stored in three successive addresses starting with the 0 address in the $\phi(\tau)$ area according to the program stored in the ROM 162, that is, successively from the addresses 0, 1, 2: 1, 2, 3: 2, 3, 4: ..., averages the data, and successively stores the data in a given area in the RAM 163. Variations in the signal $\phi(\tau)$ are thus smoothed to improve a subsequent processing accuracy.

In a step 102, the CPU 161 reads the smoothed signal $\phi(\tau)$ and data from adjacent addresses starting with the 0 address, compares them to find the difference or coincidence in level, and stores data indicative of +, 0, − in a corresponding area in the RAM 163. The smoothed signal $\phi(\tau)$ is therefore differentiated.

Figure 5:
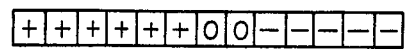
FIGS. 5, 6 and 7 are diagrams showing operation of the post-processor.

In a step 103, the CPU 161 compares variation patterns of the signs +, 0, − in the 256 addresses which are produced by the differentiation with a plurality of peak patterns stored in the ROM 162, and if any peak patterns coincide, stores the address storing such a peak in the RAM 163. The ROM 162 stores a plurality of peak patterns which can be of a main max. varying as a plurality of +'s, 0's, and −'s as shown in FIG. 5 by way of example.

Figure 6:
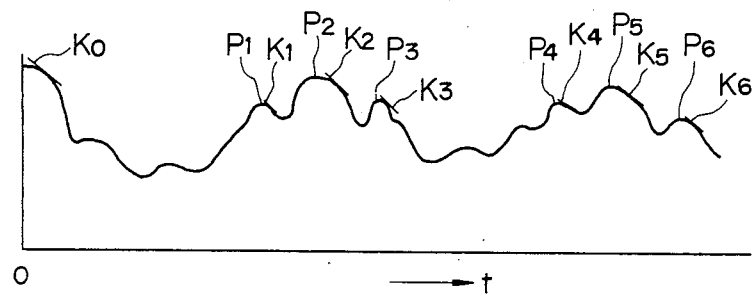
Figure 7:
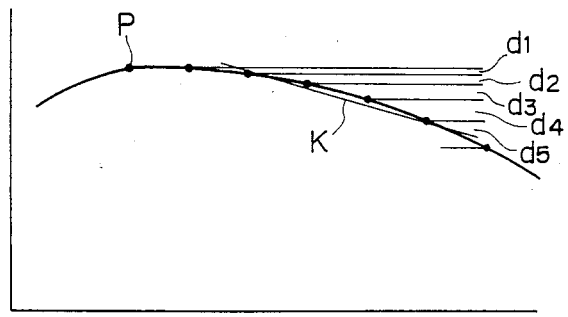

In a step 104, if six peaks $P_1$ through $P_6$ which can be of a main max. as shown in FIG. 6 are detected, then righthand slants or inclinations $k_1$ through $k_6$ for the points and a righthand inclination $k_0$ for the origin are successively calculated. To this end, the CPU 161 calculates the differences $d_1, d_2, d_3, d_4, d_5$ between data in five successive addresses and those in adjacent successive addresses, starting successively from an address adjacent to a peak, in order to increase the accuracy of calculation of the inclinations, and then calculates a righthand inclination k by averaging the differences according to $(d_1+d_2+d_3+d_4+d_5)/5$ (see FIG. 7).

In a step 105, the CPU 161 subtracts the righthand inclination $k_0$ successively from the righthand inclinations $k_1$ through $k_6$, and stores the addresses of the peaks $P_2$ and $P_5$ with the differences being in the range of from 0.75 to 1.25, as main max. in the RAM 163.

In a step 106, the CPU 161 effect various screening processes for an increased accuracy in determining the first main max. $P_2$ as a heartbeat interval. The CPU 161 determines the address $X_2$ of the first main max. $P_2$ and determines if the address coincides with or approximates the address of the second main max. $P_3$. Furthermore, the CPU 161 determines if the address of $P_2$ as converted into FHR is in the range of from 50 to 210 beat/min.

The CPU 161 then subtracts the address of the first main max. stored in the RAM 163 and detected by the immediately prior post-processing, and determines if the difference as converted into FHR is in the range of ±15 beats/min. If the first main max. $P_2$ clears all of the screening references, the address thereof is delivered to the D/A converter 17, and stored in the RAM 163 for the screening of next post-processing after 320 ms.

With the above post-processing, though the fetal heartbeat signal f(t) as autocorrelated varies in a complex pattern, a heartbeat interval can accurately be detected as a digital address signal. Since the address signal corresponds to a time interval between adjacent heartbeats, the signal is converted into a heart rate per minute, which is then converted by the D/A converter 17 into a step-like signal of a corresponding level. The step-like signal as well as the labor signal is recorded on a recording chart by the recorder 18.

Therefore, an approximate waveform can be detected more accurately, since one of the waveforms to be compared is fixed, than the conventional case in which two waveforms of relatively high level are detected from any peaks and an interval between the detected waveforms is calculated. The accuracy is also improved by comparing righthand inclinations or post peak slopes not based on the peak level.

Although a certain preferred embodiment has been shown and described, it should be understood that many changes and modifications may be made therein without departing from the scope of the appended claims.

What is claimed is:

1. A method of detecting a fetal heart rate, comprising the steps of:
   (a) emitting an ultrasonic wave to a fetal heart and converting a signal reflected by the fetal heart into an electric signal with a transducer;
   (b) detecting a frequency-shifted signal from the converted electric signal as a fetal heartbeat signal;
   (c) forming an autocorrelation function of the detected fetal heartbeat signal;
   (d) detecting peaks of the autocorrelation function;
   (e) calculating a righthand inclination of the origin of the autocorrelation function and righthand inclinations of the detected peaks;
   (f) detecting one of the peaks which has an inclination close to that of the origin and is closest to said origin; and (g) issuing a signal indicative of a delay time of said closest peak with respect to said origin.

2. A method according to claim 1, including the step of effecting screening based on an additional decision standard prior to said step of issuing the signal.

3. An apparatus for detecting a fetal heart rate, comprising:
(a) a transducer for receiving an ultrasonic signal reflected by a fetal heart and converting the same into an electric signal;
(b) pre-processor means for generating a fetal heartbeat signal by effecting AM detection on a frequency-shifted signal in the signal detected by said transducer;
(c) an autocorrelator for forming an autocorrelation function of an output signal from said pre-processor means as a digital signal;
(d) memory means for storing the autocorrelation function signal issued periodically from said autocorrelator into an address corresponding to its delay time;
(e) means for detecting peaks of the signal stored in said memory means;
(f) means for calculating a righthand inclination of the origin of the autocorrelation function and righthand inclinations of the detected peaks;
(g) means for comparing the righthand inclination of said origin and the righthand inclinations of the peaks to detect said address of the peak within a predetermined error; and
(h) means for issuing an address signal of a true peak closest to the address of said origin among said addresses detected by said detecting means as a signal indicative of a heartbeat interval.

4. An apparatus according to claim 3, wherein said peak detecting means includes means for comparing a plurality of peak patterns which can be of a true peak and are stored in another memory with said autocorrelation function signal.

5. An apparatus according to claim 3, wherein said issuing means includes screening means for determining the address of the true peak closest to the address of the origin before the address of the true peak is issued.

6. An apparatus according to claim 3, 4, or 5, further including D/A converter means for converting the peak address signal issued from said issuing means into an analog signal and supplying said analog signal to a recorder.

7. A method of detecting a fetal heart rate, comprising the steps of:
(a) emitting an ultrasonic wave to a fetal heart and converting a signal reflected by the fetal heart into an electric signal with a transducer;
(b) detecting a frequency-shifted signal from the converted electrical signal as a fetal heartbeat signal;
(c) forming an autocorrelation function of the detected fetal heartbeat signal;
(d) detecting peaks of the autocorrelation function;
(e) calculating the slope at a predetermined point of the origin of the autocorrelation function and the slope at a corresponding point of the detected peaks;
(f) detecting one of the peaks which has a slope similar to that of the origin and is closest to said origin; and
(g) issuing a signal indicative of a time delay of said closest peak with respect to said origin.

8. The invention in accordance with claim 7 wherein the slope is determined at a post-peak point.

9. The invention in accordance with claim 8 wherein screening is provided by the use of an additional decision standard prior to the step of issuing a signal.

10. An apparatus for detecting a fetal heart rate, comprising:
(a) a transducer for receiving an ultrasonic signal reflected by a fetal heart and converting the same into an electric signal;
(b) pre-processor means for generating a fetal heartbeat signal by effecting AM detection of a frequency-shifted signal and the signal detected by said transducer;
(c) autocorrelator for forming an autocorrelation function of an output signal from said pre-processor means as a digital signal;
(d) memory means for storing the autocorrelation function signal issued periodically from said autocorrelator into an address corresponding to its delay time;
(e) means for detecting peaks of the signal stored in said memory means;
(f) means for calculating the slope of a predetermined point of the origin of the autocorrelation function and the slope of corresponding predetermined points of the detected peaks;
(g) means for comparing the slope of said origin and the slopes of the peaks to detect the address of the peak within a predetermined error; and
(h) means for issuing an address signal of a true peak closest to the address of said origin among said addresses detected by said detecting means as a signal indicative of a heartbeat interval.

11. The invention in accordance with claim 10 wherein the slope is determined at a post-peak point with respect to said origin and said detected peaks.

12. The invention in accordance with claim 11 wherein said peak detecting means includes means for comparing a plurality of peak patterns stored in a memory with said autocorrelation function signal.

13. The invention in accordance with claim 12 wherein the screening means determines if the address of the true peak closest to the address of the origin is in the range of from approximately 50–210 beats per minute and thereafter subtracts the address of the previous peak and determines if the difference is in the range of ±15 beats per minute.

14. The invention in accordance with claim 11 wherein D/A converter means is provided for converting the peak address system issued from said issuing means into an analog signal and supplying said analog signal to a recorder.

15. The invention in accordance with claim 10 wherein said issuing means includes screening means for determining the address of the true peak closest to the address of the origin before the address of the true peak is issued.

* * * * *